United States Patent [19]
Hammen et al.

[11] 4,064,272
[45] Dec. 20, 1977

[54] 2-AMINOMETHYLENEINDANONE ANALGESIC AGENTS

[75] Inventors: Philip D. Hammen, East Lyme; George M. Milne, Jr., Waterford, both of Conn.

[73] Assignee: Pfizer Inc., New York, N.Y.

[21] Appl. No.: 763,241

[22] Filed: Jan. 27, 1977

Related U.S. Application Data

[62] Division of Ser. No. 312,693, Dec. 6, 1972, Pat. No. 4,022,836.

[51] Int. Cl.² ............................................. A61K 31/135
[52] U.S. Cl. ..................................................... 424/330
[58] Field of Search ........................................ 424/330

[56] References Cited

U.S. PATENT DOCUMENTS 3,454,565  7/1969  Safir .................................. 260/570.8

OTHER PUBLICATIONS

Wanzlick et al., "Chemical Berichte", vol. 96, pp. 3024–3027 (1963).

*Primary Examiner*—Stanley J. Friedman
*Attorney, Agent, or Firm*—Connolly and Hutz

[57] ABSTRACT

Novel 2-aminomethyleneindanones having analgesic activity are disclosed.

2 Claims, No Drawings

2-AMINOMETHYLENEINDANONE ANALGESIC AGENTS

CROSS REFERENCE TO RELATED APPLICATION

This application is a divisional of application Ser. No. 312,693 filed Dec. 6, 1972 now U.S. Pat. No. 4,022,836.

BACKGROUND OF THE INVENTION

This invention relates generally to new chemical compounds which are useful as analgesic agents. More particularly, it is concerned with novel 2-aminomethyleneindanones which exhibit superior analgesic action without possessing high toxicity.

SUMMARY OF THE INVENTION

The novel compounds of the invention have the formula:

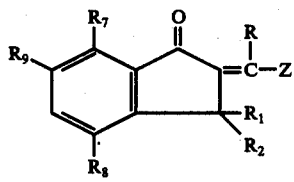

and the pharmaceutically-acceptable acid addition salts thereof, wherein R is hydrogen, lower alkyl or phenyl;

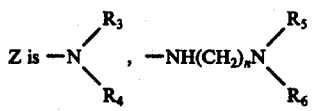

or $-NH(CH_2)_nOR_3$, wherein $R_3$ and $R_4$ are each hydrogen or lower alkyl, $R_5$ and $R_6$ are lower alkyl and $n$ is an integer of from 1 to 5; $R_1$ and $R_2$ are hydrogen or lower alkyl; $R_7$ and $R_8$ are each hydrogen, fluoro or chloro; and $R_9$ is hydrogen or fluoro. Those compounds wherein Z is

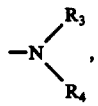

particularly 2-aminomethylene-1-indanone, are preferred.

A method of alleviating pain utilizing the novel compounds of the invention is also provided.

DETAILED DESCRIPTION OF THE INVENTION

The compounds of the invention may be prepared by the treatment of a 1-indanone with ethyl formate and sodium methoxide in benzene to yield on acid workup, a 2-hydroxymethylene-1-indanone. The 1-indanone may be appropriately substituted as in formula I wherein $R_1$ and $R_2$ are hydrogen or lower alkyl; $R_7$ and $R_8$ are each hydrogen, fluoro or chloro; and $R_9$ is hydrogen or fluoro. The term lower alkyl as used in this specification is meant to include chains of from 1 to 4 carbon atoms.

The 2-hydroxymethylene-1-indanone is then reacted with the appropriate nitrogen compound e.g. ammonium acetate, dimethyl amine, monomethyl amine or aminoethanol, in ethanol or any other suitable solvent to yield a 2-aminomethylene-1-indanone which is then dried and recrystallized from benzene or any other suitable solvent.

Alternatively, the compounds of the invention may be prepared by treatment of the 1-indanone with the appropriate N,N-dimethyl carboxylic acid amide acetal, $RC(OCH_3)_2NMe_2$ or $RC(OC_2H_5)_2NMe_2$, in ethanol or any other suitable solvent to give the corresponding 2-dimethylaminomethylene-1-indanone. This compound is then reacted with the appropriate nitrogen compound, e.g. ammonium carbonate, monomethylamine or aminoethanol, in ethanol or any other suitable solvent to yield a 2-aminomethylene-1-indanone.

Acid addition salts may be readily prepared simply by dissolving the free base in a suitable solvent, e.g. acetone, water, or a lower aliphatic alcohol (ethanol, isopropanol), containing the desired acid, or to which the desired acid is subsequently added. The salts are recovered by filtration, precipitation with a non-solvent, by evaporation of the solvent or, in the case of aqueous solutions, by lyophilization.

Acids from which pharmaceutically-acceptable addition salts of the compounds of the invention can be prepared are those which form non-toxic acid addition salts containing pharmaceutically-acceptable anions, such as the hydrochloride, hydrobromide, hydroiodide, sulfate or bisulfate, phosphate or acid phosphate, acetate, maleate, fumarate, lactate, citrate, gluconate, saccharate and p-toluene sulfonate salts.

The analgesic activity of these compounds was evaluated by means of tests using thermal nociceptive stimuli, a test using pressure nociceptive stimuli and a test using chemical nociceptive stimuli.

The thermal nociceptive stimuli tests run were the mouse hot plate analgesic test, modified after Woolfe and MacDonald (J. Pharmacol, Exp. Ther., 80:300-307, 1944) and the mouse tail flick analgesic test, modified after D'Amour and Smith (J. Pharmacol. Exp. Ther., 72:74-79, 1941).

The pressure nociceptive stimuli test run was a modification of the tail pinch test as described by Haffner (Deutsch Med. Wschr., 55:731-732, 1929).

The chemical nociceptive stimuli test run was the suppression of irritant-induced writhing, modified after Siegmund et al. (Proc. Soc. Exp. Bio., 95:729, 1957).

The compounds of the invention can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules either alone or in admixture with excipients or in the form of elixirs or suspensions containing flavoring or coloring agents. They may be injected parenterally, for example, intramuscularly or subcutaneously. For parenteral administration, they are best used in the form of a sterile aqueous solution which may contain other solutes, for example, enough salts or glucose to make the solution isotonic.

With respect to dosage levels, a broad dosage range of 25 to 500 mg. for adults is appropriate, a particularly preferred range being from 50 to 150 mg., such dosage being administrable up to four times a day. The physician in any event will determine the actual dosage which will be most suitable for an individual patient and it will vary with age, the weight and response of the particular patient. The above dosages are exemplary of the average host. There can, of course, be individual cases where higher or lower dosage ranges are merited, and such are within the scope of this invention.

The invention is illustrated by the following Examples.

EXAMPLE I

Preparation of 2-Hydroxymethylene-1-Indanone

To a mechanically stirred suspension of ethyl formate (600 ml.) and sodium methoxide (430.0 gm., 7.95 mole) in 3.7 liters of dry benzene, in a nitrogen charged 22 liter round bottom flask, cooled with an ice/$H_2O$ bath to 5° C, was added 1-indanone (500 gm., 3,785 mole) dissolved in 3.5 liter of benzene. The 1-indanone was added dropwise over a period of 1.5 hrs., maintaining the reaction temperature below 8° C. The color of the reaction mixture gradually changed from tan to a dark, purple-black over the course of the addition with the formation of a precipitate. Upon completion of the addition the ice-bath was removed and the reaction mixture was allowed to warm to approximately 15° C over 4.5 hours. The viscous, purple-black reaction mixture was hydrolyzed by the addition of ice/water, diluted with an equal volume of water and heated in a steam bath to 50° C giving a black solution. The benzene layer was separated and washed with 1 liter of 5% sodium hydroxide. The wash was added to the aqueous layer and back extracted with two 2 liter portions of ether.

The above reaction procedure was repeated two more times.

The combined aqueous layers from the three reactions were poured onto an ice/HCl mixture (10.7 liters 12NHCl) giving an off white precipitate which in filtration and air drying (15–20 min.) gave a water wet cake (3.7 kg.) of 2-hydroxymethylene-1-indanone, m.p. 115°–116° C (Lit m.p. 112°–113° C, J. Amer. Chem. Soc., 66:218, 1944). This product was sufficiently pure for the subsequent reaction.

Preparation of 2-Aminomethylene-1-Indanone

To a stirred solution of 2-hydroxy-methylene-1-indanone (1.6 kg. as a 3.7 kg. wet cake) dissolved in ethanol (30 liters), and under a nitrogen atmosphere was added ammonium acetate (1.92 kg. 24.8 mole). After eight hours the reaction was complete and the ethanol was removed by vacuum distillation. The reaction mixture was cooled to room temperature and after filtration and air drying (1 hr.) yielded crude 2-aminomethylene-1-indanone (I) as orange crystals. The crystals were then dissolved in a minimum amount of hot ethanol and the solution was decolorized with activated charcoal. Crystals appeared in the filtrate and after cooling overnight at 5° C, the reaction mixture was filtered yielding 960 gm. of compound (I) as light orange crystals. The filtrate was again treated with activated charcoal and recrystallized providing an additional 200 gm. of compound (I). The combined sample (1160 gm.) was milled giving a fine yellowish powder which was dried at 50° C/25 mm/Hg for 48 hours. A sample (50 gm.) of this material was recrystallized three times from ethanol to give 2-aminomethylene-1-indanone (15 gm.), m.p. 166°–168° C.

Anal. Calc'd. for $C_{10}H_9ON$: C,75.45; H,5.70; N,8.80; Found: C,75.13; H,5.70; N,8.77.

EXAMPLES II TO XII

The following compounds were made by the procedure described in Example I, but with the use of the appropriately substituted starting materials:

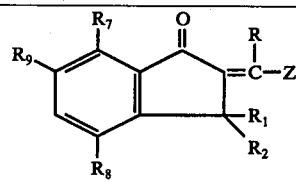

| Example | Formula | Analysis (Calculated in Brackets) | | |
|---------|---------|------|------|------|
|         |         | % C  | % H  | % N  |
| II      | $C_{11}H_{11}ON$ | 76.63 | 6.41 | 8.10 |
|         |         | (76.37 | 6.46 | 8.04) |
| III     | $C_{16}H_{13}ON$ | 81.32 | 5.41 | 5.69 |
|         |         | (81.68 | 5.57 | 5.95) |
| IV      | $C_{12}H_{13}ON$ | 76.96 | 7.05 | 7.54 |
|         |         | (76.97 | 7.00 | 7.48) |
| V       | $C_{10}H_8ONCl$ | 62.0 | 4.33 | 7.40 |
|         |         | (62.23 | 4.18 | 7.26) |
| VI      | $C_{10}H_8ONCl \cdot H_2O$ | 56.81 | 4.79 | 6.52 |
|         |         | (56.92 | 4.78 | 6.64) |
| VII     | $C_{10}H_7ONF$ | 68.47 | 3.99 | 8.04 |
|         |         | (68.64 | 4.01 | 7.96) |
| VIII    | $C_{11}H_{11}ON$ | 76.29 | 6.57 | 8.17 |
|         |         | (76.27 | 6.40 | 8.09) |
| IX      | $C_{12}H_{13}ON$ | 77.03 | 6.82 | 7.43 |
|         |         | (76.98 | 7.00 | 7.48) |
| X       | $C_{12}H_{12}ONCl$ | (64.59 | 5.39 | 6.48 |
|         |         | (65.22 | 5.47 | 6.34) |
| XI      | $C_{12}H_{12}ONCl$ | 65.38 | 5.58 | 5.99 |
|         |         | (65.02 | 5.46 | 6.32) |
| XII     | $C_{12}H_{12}ONCl$ | 60.83 | 5.17 | 5.90 |
|         |         | (60.82 | 5.10 | 5.90) |

| Example | Substituents | Crystallization Solvent | m.p. ° C |
|---------|-------------|------------------------|----------|
| II      | Z = $NH_2$; R = $CH_3$; $R_1,R_2$, $R_7,R_8,R_9$ = H | Ethyl Acetate | 172–4 |
| III     | Z = $NH_2$; R = $C_6H_5$; $R_1,R_2$, $R_7,R_8,R_9$ = H | $CH_3CN/H_2O$ | 69–71 |
| IV      | Z = $NH_2$; $R_1,R_2$ = $CH_3$; R, $R_7,R_8,R_9$ = H | Benzene | 143–5 |

-continued

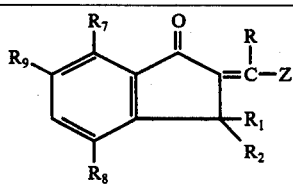

| | | | |
|---|---|---|---|
| V | Z = NH$_2$; R,R$_1$,R$_2$,R$_7$, R$_9$ = H; R$_8$ = Cl | Ethyl Acetate/Hexane | 115–9 |
| VI | Z = NH$_2$; R$_7$ = Cl; R,R$_1$, R$_2$,R$_8$,R$_9$ = H | Ethyl Acetate/Hexane | 117–20 |
| VII | Z = NH$_2$; R$_9$ = F; R,R$_1$, R$_2$,R$_7$,R$_8$ = H | Benzene | 179–82 |
| VIII | Z = NHCH$_3$; R,R$_1$,R$_2$,R$_7$, R$_8$,R$_9$ = H | None | 194–6 |
| IX | Z = N(CH$_3$)$_2$; R,R$_1$,R$_2$, R$_7$,R$_8$,R$_9$ = H | Benzene/Hexane | 157–9 |
| X | Z = N(CH$_3$)$_2$; R$_8$ = Cl; R, R$_1$,R$_2$,R$_7$,R$_8$ = H | Benzene/Hexane | 149–50 |
| XI | Z = N(CH$_3$)$_2$;R,R$_1$,R$_2$, R$_8$,R$_9$ = H; R$_7$ = Cl | Benzene/Hexane | 183–5 |
| XII | Z = NHCH$_2$CH$_2$OH; R$_8$ = Cl; R,R$_1$,R$_2$,R$_7$,R$_9$ = H | Isopropyl Alcohol | 164–6 |

EXAMPLE XIII

Preparation of 2-Dimethylaminomethylene-1-indanone

To a 2 liter 3-neck round-bottomed flask equipped with a reflux condenser and magnetic stirrer were added 50.0 gm. (0.38 mole) of 1-indanone, 750 ml. of ethanol and 67.8 gm. (0.57 mole) of N,N-dimethylformamide dimethylacetal under a nitrogen atmosphere. The resulting solution was boiled under reflux for 5 hrs. and stirred overnight at room temperature. The reaction mixture was then taken up in 1 l. of hot benzene, treated with activated charcoal, filtered, and allowed to crystallize. A second recrystallization from benzene yielded 45.7 gm. of 2-dimethylaminomethylene-1-indanone, m.p./159°–161° C. An additional 18.3 gm., m.p. 157°–60° C, was recovered from the mother liquors of the first crystallization.

A sample of 2-dimethylaminomethylene-1-indanone, m.p. 157°–59° C from benzene/hexane, which was prepared in a similar manner was analyzed.

Anal. Calc'd. for C$_{12}$H$_{13}$ON: C, 76.98; H, 7.00; N, 7.48; Found: C, 77.03; H, 6.82; N, 7.43.

Preparation of 2-Aminomethylene-1-indanone

A mixture of 54.0 gm. (0.29 mole) of 2-dimethylaminomethylene-1-indanone, 255 gm. of ammonium carbonate, 900 ml. of ammonium hydroxide, and 450 ml. of ethanol was stirred at room temperature for 6 days, then concentrated to about 700 ml. and poured onto 1500 ml. of cold water. The resulting solid was filtered and dried at 50° C (25 mm.) to give 45.4 gm. of impure 2-aminomethylene-1-indanone, m.p. 159°–60° C, which was partitioned between 2 liters of ethyl acetate and 1 liter of water to remove any remaining inorganic salts. The ethyl acetate layer was dried over magnesium sulfate, filtered and concentrated under reduced pressure to give a solid which was recrystallized from ethyl acetate/acetone to yield 28.1 gm. of yellow crystals of 2-aminomethylene-1-indanone, m.p. 163°–65° C.

Anal. Calc'd. for C$_{10}$H$_9$ON: C, 75.45; H, 5.70; N, 8.80; Found: C, 75.31; H, 5.77; N, 8.83.

EXAMPLE XIV

Preparation of 5-chloro-2-dimethylaminomethylene-1-indanone

A solution of 10.0 gm. (0.06 mole) of 4-chloro-1-indanone and 10.7 gm. (0.09 mole) of N,N-dimethylformamide dimethylacetal in 250 ml. of absolute alcohol was boiled under reflux for 20 hrs., then an additional 5.35 gm. (0.045 mole) of N,N-dimethylformamide dimethylacetal was added. The reaction mixture was refluxed for an additional 5 hrs., cooled, and concentrated under reduced pressure to give a red solid which was taken up in benzene, treated with activated charcoal, filtered, and evaporated under reduced pressure to give a light red solid. Two more recrystallizations from benzene/hexane gave 8.3 gm. of 5-chloro-2-dimethylaminomethylene-1-indanone, m.p. 148°–149.5° C.

One additional recrystallization from benzene gave an analytical sample, m.p. 149°–50° C.

Anal. Calc'd. for C$_{12}$H$_{12}$ONCl; C, 65.22; H, 5.47; N, 6.34; Found: C, 64.59; H, 5.39; N, 6.48.

Preparation of 5-chloro-2-(2-hydroxyethyl)aminomethylene-1-indanone

A solution of 1.5 gm. (0.007 mole) of 5-chloro-2-dimethylaminomethylene-1-indanone, 1.3 gm. (0.021 mole) of 2-aminoethanol, 5 drops of acetic acid, and 20 ml. of ethanol was stirred overnight at room temperature under a nitrogen atmosphere. The pink precipitate was filtered, washed with a small amount of ethanol, and recrystallized from isopropyl alcohol to give 0.80 gm. of white crystals of 5-chloro-2-(2-hydroxyethyl)aminomethylene-1-indanone, m.p. 164°–166° C.

Anal. Calc'd for C$_{12}$H$_{12}$NCl: C, 60.82; H, 5.10; N, 5.91; Found: C, 60.83; H, 5.17; N, 5.90.

EXAMPLE XV

Following the procedure described in Example I, but using the appropriately substituted starting materials the following compounds may be made.

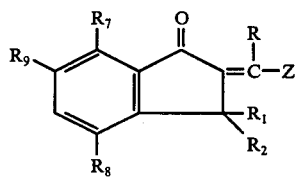

Z = NH$_2$; R, R$_1$, R$_2$, R$_8$, R$_9$ = H; R$_7$ = F
Z = N(CH$_3$)$_2$; R, R$_1$, R$_2$, R$_7$, R$_9$ = H; R$_8$ = F
Z = N(n-C$_4$H$_9$)$_2$; R, R$_1$, R$_2$, R$_7$, R$_8$, R$_9$ = H
Z = N(C$_2$H$_5$)$_2$; R, R$_1$, R$_2$, R$_7$, R$_8$, R$_9$ = H
Z = NH$_2$; R, R$_7$, R$_8$, R$_9$ = H; R$_1$, R$_2$, = n−C$_4$H$_9$
Z = NH(CH$_2$)$_5$NH$_2$; R, R$_1$, R$_2$, R$_7$, R$_8$, R$_9$ = H
Z = NH(CH$_2$)$_2$NHCH$_3$; R, R$_1$, R$_2$, R$_8$, R$_9$ = H; R$_7$ = Cl
Z = NHCH$_2$NH$_2$; R, R$_1$, R$_2$, R$_7$, R$_8$, R$_9$ = H
Z = NHCH$_2$OH; R, R$_1$, R$_2$, R$_7$, R$_8$, R$_9$ = H
Z = NH(CH$_2$)$_5$OH: R, R$_1$, R$_2$, R$_7$, R$_8$, R$_9$ = H
Z = NHCH$_2$OCH$_3$; R, R$_1$, R$_2$, R$_7$, R$_9$ = H; R$_8$ = Cl

The above compounds may also be prepared by the procedure described in Example XIII but using the appropriately substituted starting materials.

EXAMPLE XVI

The following tests were run in order to indicate the analgesic properties of the compounds of the invention Mouse hot plate analgesic test (HP)

The method used was modified after Woolfe and MacDonald (1944). A controlled heat stimulus was applied to the feet of mice on a one-eighth inch thick aluminum plate. A 250 w reflector infrared heat lamp was placed under the bottom of the aluminum plate; a thermal regulator, connected to thermistors on the plate surface, programmed the heat lamp to maintain a constant temperature of 57° C. Each mouse was dropped into a 6½ D. glass cylinder resting on the hot plate, and timing began when the animal's feet touched the plate. The mouse was observed at 0.5 and 2 hr. after treatment with test compound, for the first "flicking" movements of one or both hind feet, or until 10 sec. elapsed without such movements.

Mouse tail flick analgesic test (TF)

The tail flick test in mice was modified after D'Amour and Smith (1941), using controlled high intensity heat applied to the tail.

Each mouse was placed in a snug-fitting metal cylinder, with the tail protruding through one end. This cylinder was arranged so that the tail lay flat over a concealed heat lamp. At the onset of testing, an aluminum flag over the lamp was drawn back, allowing the light beam to pass through the slit and focus onto the end of the tail. A timer was simultaneously activated. The latency of a sudden flick of the tail was ascertained. Untreated mice usually reacted from 3-5 sec. after exposure to the lamp. The end point was 10 sec. Each mouse was tested at 0.5 and 2 hr. after drug treatment.

Effect on the Haffner tail pinch procedure (RTC) A modification of the procedure of Haffner (1929) was used to ascertain the effects of test compounds on aggressive attacking responses elicited by a stimulus pinching the tail. A Johns Hopkins 2½ inches "bulldog" clamp was clamped onto the root of the rat's tail prior to drug treatment, and again at 0.5, 1 and 2 hr. after drug treatment. The endpoint at each trial was clear attacking and biting behavior directed towards the offending stimulus; the clamp was removed to 30 sec. if attacking had not occurred by then, and the latency of response was recorded as 30 sec.

Suppression of irritant-induced writhing (PBQ)

A group of 10 to 20 mice were pretreated subcutaneously with saline or with test compounds. One hour later each group was treated with phenylbenzoquinone (2 mg/kg; 5% in ethanol), an intraperitoneal irritant known to produce writhing (repetitive abdominal contractions). At 10 minutes after phenylbenzoquinone administration, known to correspond to peak writhing time, the mice were observed for 2 min. for the presence or absence of writhing.

The results obtained are as follows:

| Compound | HP Test % Protected | | TF Test % Protected | | RTC Test % Protected | | | PBQ - % Protected at 100 mg/kg |
|---|---|---|---|---|---|---|---|---|
| | 0.5 hr | 2 hr | 0.5 hr | 2 hr | 0.5 hr | 1 hr | 2 hr | |
| I | 40 | 80 | 10 | 60 | >30 | >30 | >30 | 40 |
| II | 20 | 20 | 10 | 0 | >30 | >30 | >30 | — |
| III | 40 | 40 | 10 | 0 | 4 | 4 | 6 | — |
| IV | 30 | 0 | 50 | 0 | — | | | 0 |
| V | 40 | 0 | 80 | 15 | 13 | 3 | 3 | 0* |
| VI | 100 | 60 | 80 | 0 | >30 | >30 | >30 | 60 |
| VII | 80 | 20 | 40 | 0 | >30 | 10 | 11 | 20 |
| VIII | 40 | 40 | 20 | 20 | — | | | 40 |
| IX | 40 | 20 | 20 | 0 | >30 | >30 | >30 | 40 |
| X | 40 | 0 | 80 | 10 | >30 | >30 | >30 | 20 |
| XI | 60 | 40 | 50 | 0 | >30 | >25 | >30 | 100 |
| XII | 20 | 40 | 70 | 10 | 15 | 13 | 11 | 100* |

*at 320 mg./kg.

What is claimed is:
1. A method of alleviating pain comprising the administration to a pain afflicted host of a pain alleviating effective amount of a compound of the formula:

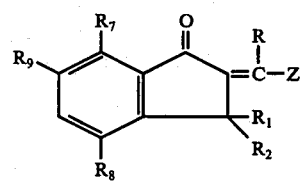

or a pharmaceutically-acceptable acid addition salt thereof, wherein R is hydrogen, lower alkyl or phenyl;

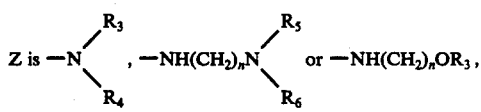
wherein $R_3$ and $R_4$ are each hydrogen or lower alkyl, $R_5$ and $R_6$ are lower alkyl and $n$ is integer of from 1 to 5; $R_1$ and $R_2$ are hydrogen lower alkyl; $R_7$ and $R_8$ are each hydrogen, fluoro or chloro; and $R_9$ is hydrogen or fluoro.
2. The method of claim 1 wherein said compound is 2-aminomethylene-1-indanone.
* * * * *

UNITED STATES PATENT AND TRADEMARK OFFICE
CERTIFICATE OF CORRECTION

PATENT NO. : 4,064,272
DATED : DECEMBER 20, 1977
INVENTOR(S) : HAMMEN ET AL

It is certified that error appears in the above—identified patent and that said Letters Patent are hereby corrected as shown below:

Claim 1, column 10 line 2, insert --or-- after "hydrogen".

Signed and Sealed this

Twentieth Day of June 1978

[SEAL]

Attest:

RUTH C. MASON
Attesting Officer

DONALD W. BANNER
Commissioner of Patents and Trademarks